United States Patent [19]

Harada et al.

[11] Patent Number: 4,530,365
[45] Date of Patent: Jul. 23, 1985

[54] PHYSIOLOGICAL SIGNAL AMPLIFIER CIRCUITRY

[75] Inventors: Hajime Harada, Tokyo; Takeshi Kojima, Saitama, both of Japan

[73] Assignee: Nihon Kohden Corporation, Tokyo, Japan

[21] Appl. No.: 517,512

[22] Filed: Jul. 26, 1983

[51] Int. Cl.³ .............................................. A61B 5/04
[52] U.S. Cl. .................................... 128/696; 128/902
[58] Field of Search ............... 128/695, 696, 709, 710, 128/902

[56] References Cited

U.S. PATENT DOCUMENTS

| | | | |
|---|---|---|---|
| 3,757,778 | 9/1973 | Graham | 128/902 |
| 3,868,948 | 3/1975 | Graetz | 128/709 |
| 3,880,146 | 4/1975 | Everett et al. | 128/710 |
| 3,991,748 | 11/1976 | Ohlsson | 128/709 |

Primary Examiner—William E. Kamm
Attorney, Agent, or Firm—Hoffmann, Dilworth, Barrese & Baron

[57] ABSTRACT

The purpose of the present invention is to provide a physiological signal amplifier circuitry exhibiting higher common mode rejection ratio with no necessity of adjustment. To realize this, outputs of the differential amplifiers are average to produce reference potential which is supplied, through a high gain amplifier, to invert terminals of the same differential amplifier as well as to invert terminals of other differential amplifiers connected to other electrodes. In the embodiment employed for the electrocardiograph, the reference potential is produced by the differential amplifier connected to extremity electrodes, and other differential amplifiers are connected to the chest electrodes.

4 Claims, 3 Drawing Figures

PHYSIOLOGICAL SIGNAL AMPLIFIER CIRCUITRY

FIELD OF THE INVENTION

The present invention relates to a physiological signal differential amplifying circuitry exhibiting the common mode rejection ratio of higher degree with no necessity of adjustment.

BACKGROUND OF THE INVENTION

In conventional physiological signal amplifying circuitry, the action potential picked up by a plurality of electrodes attached to a body is routed, through a buffer amplifier, to the lead selector which produces a desired lead signals by combining input action potential, the output of the selector being supplied to the first stage of the differential amplifiers. In such amplifier circuitry, in order to increase the common mode rejection ratio, it is necessary to make fine adjustment of the resistors for removing the common mode signals within the differential amplifiers. In addition, when the electronic switches are employed in the lead selector, variety of internal resistances of the electronic switches causes variation of the common mode rejection ratio.

SUMMARY OF THE INVENTION

It is an object of the present invention to provide a physiological signal amplifier circuitry which has been improved with respects to the aforementioned demerits.

According to the present invention, the action potential signals picked up by a plurality of electrodes selected as reference ones are supplied to non-invert input terminals of the respective differential amplifiers. The potential differences between the output terminal of the respective differential amplifiers and the ground are averaged and the averaged potential is supplied to an amplifier with high gain, output of which is the reference potential. The reference potential is supplied to the invert terminals of the aforementioned differential amplifiers as well as to the differential amplifiers of all other leads than those selected as reference ones. In such a manner the common mode rejection ratio of higher degree is obtained with no necessity of adjustment.

The above and other objects, features and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
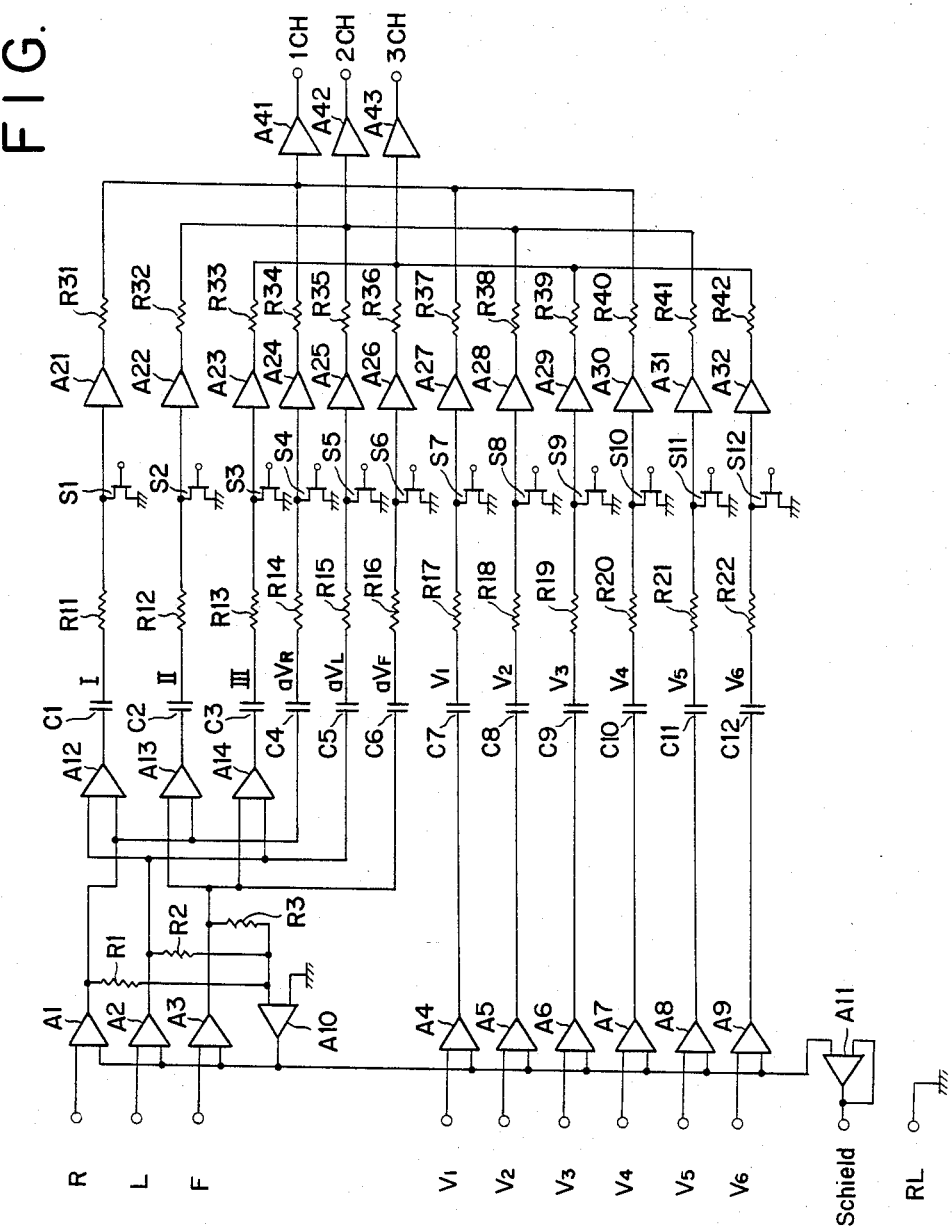
FIG. 1 is a circuit diagram of a physiological signal amplifier circuit according to the present invention, as incorporated in an electrocardiograph.

In FIG. 1, A1 through A9 are the operational differential amplifiers connected to a plurality of electrodes attached to a body. Among these differential amplifiers, A1–A3 have non-invert input terminals connected to electrodes attached to a right arm (R), a left arm (L), and a left leg (F) of the body for receiving the respective lead potential from these electrodes. The differential amplifiers A4–A9 have non-invert input terminals connected to electrodes $V_1$–$V_6$ attached to the chest. A feedback differential amplifier A10 has a higher voltage gain than that of the differential amplifiers A1–A3. Outputs from the differential amplifiers A1–A3 are averaged by resistors R1, R2, R3. The averaged voltage is then amplified by the differential amplifier A10, and the amplified output is fed to the invert input terminals of the differential amplifiers A1–A3 as a kind of negative feedback, and also fed, as a reference potential, to the invert input terminals of the differential amplifiers A4–A9. To additionally increase of the common mode rejection ratio, the output from the amplifier A10 is fed back by a buffer amplifier A11 to the sheaths of shielded wires used as input signal lines for all leads.

Differential amplifiers A12–A14 serve to differentially amplify the outputs from the differential amplifiers A1–A3 and produce lead I, II, III signals. The coupling capacitors C1–C12 are for eliminating DC components of the outputs from the differential amplifiers A12–A14 and A4–A9 thus producing the lead signals I, II, III, $_aV_R$, $_aV_L$, $_aV_F$, V1–V6 without DC components. The FET electronic switches S1–S12 contitute the lead selector circuit which shorts the undesired lead signal to the ground through R11–R22 and transmits the desired signals to the next stage. The outputs of electronic switches S1–S12 are supplied to the buffer DC amplifiers A21–A32. A ground terminal RL is normally connected to the right leg of the body and serves to keep the body at the same potential as ground. Adder resistors R31–R42 are grouped into three groups of (R31, R34, R37, R40), (R32, R35, R38, R41) and (R33, R36, R39, R42) each constituting the respective adder circuits. The first adder circuit consisting of R31, R34, R37 and R40 feeds its output to the amplifier A41 for the first channel, the second adder circuit consisting of R32, R35, R38, R41 feeds its output to the amplifier A42 for the second channel, and the third adder circuit consisting of R33, R36, R39, R42 feeds its output to the amplifier A43 for the third channel.

Figure 2:
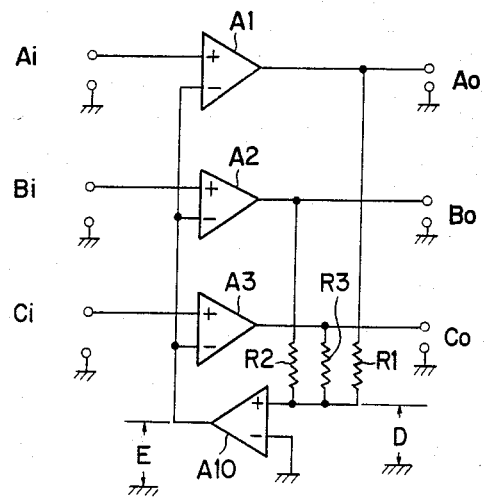
FIG. 2 is a circuit diagram of a main portion, relative to the present invention, of the physiological signal amplifier circuit shown in FIG. 1.

FIG. 2 is illustrative of the main portion, relative to this invention, of the circuit arrangement shown in FIG. 1. If the voltage gains of the differential amplifiers A1, A2 and A3 are $A_1$, $A_2$ and $A_3$ respectively, the resistance values of resistors R1, R2 and R3 are $R_1$, $R_2$, $R_3$, respectively, and the gain of the feedback amplifier A10 is $A_{10}$, and assuming that the differential amplifiers A1, A2, A3 produce output potential $A_0$, $B_0$ and $C_0$, respectively and the gain of the feedback amplifier is $A_{10}$, an input voltage D to the amplifier A10 is expressed as follows:

$$D = \frac{R_2 \cdot R_3 \cdot A_0 + R_1 \cdot R_3 \cdot B_0 + R_1 \cdot R_2 \cdot C_0}{R_1 \cdot R_2 + R_2 \cdot R_3 + R_1 \cdot R_3} \quad (1)$$

Further assuming that the output voltage from the amplifier A10 i.e. the negative feedback voltage applied to the differential amplifiers A1–A3 is E, and the non-invert input voltages to the amplifiers A1–A3 are Ai, Bi and Ci respectively, the following equations result:

$$E = A_{10} \cdot D \quad (2)$$

$$A_0 = (Ai - E)A_1 \tag{3}$$

$$B_0 = (Bi - E)A_2 \tag{4}$$

$$C_0 = (Ci - E)A_3 \tag{5}$$

Assuming that $A_1 \approx A_2 \approx A_3 \approx A$, the following equations are deduced from the equations (3)-(5):

$$B_0 = A \cdot Bi - A \cdot Ai + A_0 \tag{6}$$

$$C_0 = A \cdot Ci - A \cdot Ai + A_0 \tag{7}$$

If $R_1 \approx R_2 \approx R_3 \approx R$ in the equation (1), the following equation is established:

$$D = \frac{A_0 + B_0 + C_0}{3} \tag{8}$$

From the equations (2), (3) and (8), the following equation is deduced.

$$A_0 = (Ai - E) A_1 = (Ai - A_{10}D)A \tag{9}$$

$$= \left( Ai - A_{10} \cdot \frac{A_0 + B_0 + C_0}{3} \right) A$$

If $1/A_{10} < A$, the following formula results from the equations (6), (7) and (9):

$$A_0 \approx \frac{2A}{3} \left( Ai - \frac{Bi + Ci}{2} \right) \tag{10}$$

Likewise, $$B_0 \approx \frac{2A}{3} \left( Bi - \frac{Ai + Ci}{2} \right) \tag{11}$$

$$C_0 \approx \frac{2A}{3} \left( Ci - \frac{Ai + Bi}{2} \right) \tag{12}$$

From the equations (10) and (3) the following equations result.

$$E = A_0 \cdot A_{10}, A_0 = (Ai - E) = A(Ai - A_0 \cdot A_{10})$$

For example, if A is 20 and $A_{10}$ is $10^5$ for the transmission function $A_0/Ai = A/(1 + A \cdot A_{10})$, then transmission function for in-phase signals such as AC line interference becomes $10^{-5}$. On the other hand, from the equations (10)-(12), the transmission function for electrocardiographic signals becomes $\frac{2}{3} \times 20$. Since the potentials Ai, Bi, Ci are led from the electrodes R, L and F, respectively, the potential $A_0$, $B_0$, $C_0$ become the lead signals $_aV_R$, $_aV_L$, $_aV_F$, respectively, in which in-phase signals have been eliminated.

Since the inputs of the differential amplifiers A12-A14 shown in FIG. 1 are differential signals from the potential $A_0$, $B_0$ and $C_0$ from equations (10)-(12), the differential signals are expressed as follows:

$B_0 - A_0 = A(Bi - Ai)$, $C_0 - A_0 = A(Ci - Ai)$, and $C_0 - B_0 = A(Ci - Bi)$, and thus the leads I, II, III signals are supplied to the differential amplifiers A12-A14 respectively.

Furthermore from the equations (2)-(5) and (8), $$E = \frac{Ai + Bi + Ci}{3} \tag{13}$$

Therefore, the potential E becomes the averaged value of the potential Ai, Bi and Ci, i.e. a referential potential for the electrocardiographic signals. The potential E is commonly applied to all of the invert input terminals of the differential amplifiers A4-A9 to produce the chest lead signals $V_1$-$V_6$.

The twelve lead signals applied to the coupling capacitors C1-C12 are usually grounded through the respective series-connected resistors R11-R22 under ON condition of the electronic switches S1-S12. When any one of the electronic switches corresponding to the four groups of lead signals allotted to the corresponding channel of the electrocardiograph, (in more detail, I, $_aV_R$, $V_1$ and $V_4$ for the first channel; II, $_aV_L$, $V_2$ and $V_5$ for the second channel; and III, $_aV_F$ and $V_6$ for the third channel) e.g., the FET electronic switch S1, S5, or S12 is supplied with selection signal at its gate, the lead I signal is delivered, through the amplifier A21 and the adder resistor R31, to the first channel amplifier A41; or the lead $_aV_L$ signal is delivered, through the amplifier A25 and the adder resistor R35, to the second channel amplifier A42, or the lead $V_6$ signal is delivered, through the amplifier A32 and the adder resistor R42, to the third channel amplifier A43.

With the electronic switches S1-S12 ON condition, the coupling capacitors C1-C12 are charged with the voltages related to the polarized voltages of the corresponding leads. When any of the electronic switches S1-S12 are turned to OFF condition, the corresponding lead signal are immediately supplied to the corresponding adder circuit resistors R31-R42. Therefore, no variation in the baseline is caused and the lead voltages, i.e., physiological signals are subjected to no interruption at the time of switching the ECG leads. Accordingly the ECG waveforms are not subject to distortion due to characteristics of the coupling capacitors C1-C12 and the electronic switches S1-S12.

It is necessary to adjust the amplifiers A21-A32 so that the voltage gain of the amplifiers A24, A25, A26 is 3/2 times greater than those of the other amplifiers (A21-A23 and A27-A32) as is clear from the equations (10)-(12); for example, if the voltage gain of the amplifiers A24, A25 and A26 is 75, the voltage gain of the other amplifiers must be 50.

Figure 3:
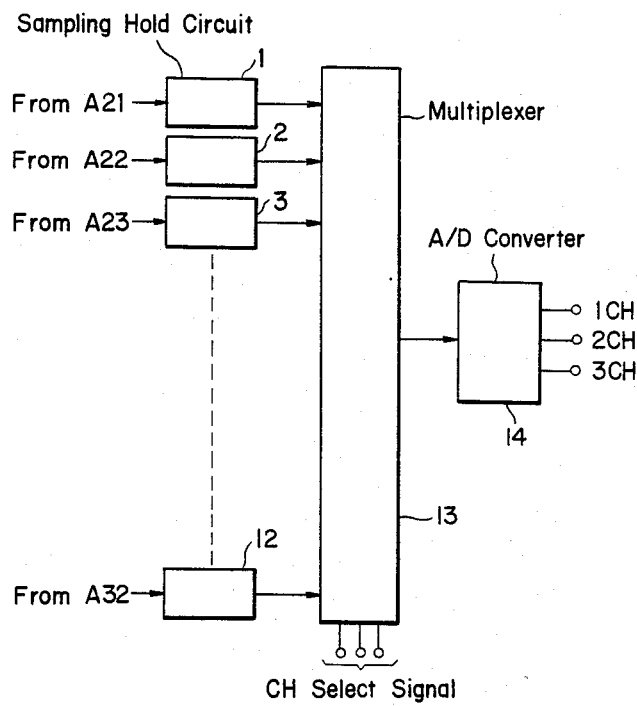
FIG. 3 is a block diagram of the later stages a modified physiological signal amplifier circuit according to the present invention as used for the analog to digital conversion.

FIG. 3 shows a modification of later stage of the amplifier circuitry in which the analog channel selector R31-R42, A41-A43 in FIG. 1 is replaced with a digital channel selector. More specifically, sampling-hold circuits 1-12 are connected to the amplifiers A21-A32 (FIG. 1), respectively, and outputs of the sampling-hold circuits are supplied to a multiplexer 13. The multiplexer 13 repeatedly scans the output signal from the sampling-hold circuits, at a high rate for a prescribed period of time, and then send the selected signals by scanning to the A/D converter 14 which converts the selected signals to corresponding digital signals. The digitized three-channel signals, in this example, are stored in a memory for use as electrocardiographic data for one of the four sequences. (The first sequence; I, II and III, the second sequence $_aV_R$, $_aV_L$ and $_aV_F$, the third sequence; $V_1$, $V_2$ and $V_3$, the fourth sequence; $V_4$, $V_5$ and $V_6$. ) After a prescribed period of time, the multiplexer 13 repeatedly scans the physiological signals of the next sequence, and again send the selected signals to the A/D converter 14 to digitize the selected signals. The digital signals thus obtained are stored in the memory for use as electrocardiographic data for every sequence.

As so far described the present invention provides a physiological signal amplifier circuitry which exhibits the common mode rejection ratio of higher degree with no necessity of adjustment by using the feedback of the averaged potential of the selected first stage amplifiers to the same amplifiers through a high gain amplifier. Additional advantageous features of the present invention have also been described.

The present invention is also applicable to an electroencephalograph. In this case the signals from the electrodes attached to both lobes of a body are used to produce reference potential. Accordingly the amplifiers A1 and A2 are used without using the amplifier A3.

Although certain preferred embodiments have been shown and described, it should be understood that many changes and modifications may be made therein without departing from the scope of the appended claims.

What is claimed is:

1. A physiological signal amplifier circuitry comprising a plurality of differential amplifiers which are connected to electrodes adapted to be located on a body to acquire action potential of the body, said differential amplifiers having a first kind of respective input terminals connected to said electrodes and a second kind of respective input terminals and including a plurality of selected differential amplifiers associated with selected ones of said electrodes, means for producing an averaged potential of output potential of said selected differential amplifiers, an amplifier for amplifying said averaged potential, said amplifier having sufficiently high gain as compared with each gain of said selected differential amplifiers and feeding its output to said second kind of input terminals of said differential amplifiers, said differential amplifiers producing potential output serving as physiological signals.

2. A physiological signal amplifier circuitry according to claim 1, wherein said amplifier for amplifying said averaged potential has higher gain by the order of $10^3$ as compared with each gain of said selected differential amplifiers.

3. A physiological signal amplifier circuitry according to claim 1, wherein said first kind of respective input terminals are connected to said electrodes by metallic shielded wires, whereby the metallic sheaths of said metallic shielded wires are fed with said ouput of said amplifier for amplifying said averaged potential through a buffer amplifier.

4. A physiological signal amplifier circuitry according to claim 1, wherein said selected ones of electrodes are adapted to be located on a right arm, a left arm, and a left leg of the body, and remaining electrodes are adapted to be located on the chest of the body for thereby acquiring electrocardiographic signals.

* * * * *

UNITED STATES PATENT AND TRADEMARK OFFICE
CERTIFICATE OF CORRECTION

PATENT NO. : 4,530,365
DATED : July 23, 1985
INVENTOR(S) : Hajime Harada and Takeshi Kojima It is certified that error appears in the above-identified patent and that said Letters Patent is hereby corrected as shown below:

Column 3, line 60, after "amplifiers" delete "Al-2-Al4" and insert "Al2-Al4".

Signed and Sealed this

First Day of October 1985

[SEAL]

Attest:

DONALD J. QUIGG

Attesting Officer

Commissioner of Patents and
Trademarks—Designate